United States Patent [19]

Wolfinbarger, Jr.

[11] Patent Number: 5,977,034
[45] Date of Patent: *Nov. 2, 1999

[54] COMPOSITION FOR CLEANING BONES

[75] Inventor: Lloyd Wolfinbarger, Jr., Norfolk, Va.

[73] Assignee: LifeNet Research Foundation, Virginia Beach, Va.

[ * ] Notice: This patent issued on a continued prosecution application filed under 37 CFR 1.53(d), and is subject to the twenty year patent term provisions of 35 U.S.C. 154(a)(2).

[21] Appl. No.: 08/620,856

[22] Filed: Mar. 20, 1996

Related U.S. Application Data

[63] Continuation-in-part of application No. 08/395,113, Feb. 27, 1995, Pat. No. 5,556,379, which is a continuation-in-part of application No. 08/293,206, Aug. 19, 1994, abandoned.

[51] Int. Cl.$^6$ .............................. C11D 1/66; C11D 1/72; C11D 1/83; A61F 2/28
[52] U.S. Cl. .......................... 510/109; 510/421; 510/422; 510/506; 623/16
[58] Field of Search .................... 510/421, 422, 510/506, 109; 252/FOR 243; 623/16

[56] References Cited

U.S. PATENT DOCUMENTS

| | | | |
|---|---|---|---|
| 4,020,183 | 4/1977 | Asculai et al. | 424/341 |
| 4,169,123 | 9/1979 | Moore et al. | 422/29 |
| 4,207,689 | 6/1980 | Romera-Sierra et al. | 35/20 |
| 4,233,174 | 11/1980 | Sheridan | 252/170 |
| 4,258,722 | 3/1981 | Sessions et al. | 128/753 |
| 4,315,919 | 2/1982 | Shanbrom | 424/177 |
| 4,366,822 | 1/1983 | Altshuler | 128/752 |
| 4,412,985 | 11/1983 | Shanbrom | 424/78 |
| 4,456,589 | 6/1984 | Holman et al. | 424/95 |
| 4,526,751 | 7/1985 | Gartner | 422/37 |
| 4,553,974 | 11/1985 | Dewajnee | 8/94.11 |
| 4,557,853 | 12/1985 | Collins | 252/128 |
| 4,637,931 | 1/1987 | Schmitz | 424/78 |
| 4,678,470 | 7/1987 | Nashef et al. | 623/16 |
| 4,695,536 | 9/1987 | Lindstrom et al. | 435/1 |
| 4,801,299 | 1/1989 | Brendel et al. | 623/1 |
| 4,891,221 | 1/1990 | Shanbrom | 424/101 |
| 4,923,677 | 5/1990 | Simon et al. | 422/37 |
| 4,946,792 | 8/1990 | O'Leary | 435/268 |
| 4,975,526 | 12/1990 | Kuberasampath et al. | 530/350 |
| 4,994,030 | 2/1991 | Glowczewskie et al. | 604/84 |
| 5,037,437 | 8/1991 | Matsen, III | 623/16 |
| 5,041,055 | 8/1991 | Roth | 452/140 |
| 5,047,030 | 9/1991 | Draenert | 606/65 |
| 5,106,626 | 4/1992 | Parson et al. | 424/423 |
| 5,118,512 | 6/1992 | O'Leary et al. | 424/549 |
| 5,120,656 | 6/1992 | O'Leary et al. | 435/268 |
| 5,133,756 | 7/1992 | Bauer et al. | 623/16 |
| 5,167,961 | 12/1992 | Lussi et al. | 424/423 |
| 5,186,945 | 2/1993 | Shanbrom | 424/529 |
| 5,192,828 | 3/1993 | Draenert | 606/65 |
| 5,333,626 | 8/1994 | Morse et al. | 604/48 |
| 5,414,144 | 5/1995 | Watanabe et al. | 568/670 |
| 5,454,815 | 10/1995 | Geisser et al. | 606/85 |
| 5,494,784 | 2/1996 | Hosaka et al. | 430/326 |
| 5,513,662 | 5/1996 | Morse et al. | 128/898 |
| 5,539,043 | 7/1996 | Kimura et al. | 524/504 |
| 5,567,348 | 10/1996 | Nozawa et al. | 510/175 |

FOREIGN PATENT DOCUMENTS

| | | |
|---|---|---|
| 540798 | 5/1957 | Canada . |
| 360743 | 5/1990 | European Pat. Off. . |
| 952189 | 8/1982 | U.S.S.R. . |
| 964545 | 7/1964 | United Kingdom . |

OTHER PUBLICATIONS

Sharma et al., "An Antiviral Agent for General Use in Biological Samples and Tissue", American Clinical Laboratory, pp. 22–33, Oct. 1990.

Lavelle et al., "Evaluation of an Antimicrobial Soap Formula for Virucidal Efficacy In Vitro againstuman Immunodeficiency Virus in a Blood–Virus Mixture", Antimicrobial Agents and Chemotherapy, vol. 33, No. 12, Dec. 1989.

McCutcheon's Emulsifiers and Detergents, 1985 International, 1985.

McCutcheon's Functional Materials, 1985 North American Edition, 1985.

McCutcheon's Emulsifiers & Detergents, 1995 North American Edition and International Edition, 1995.

Sattar et al., "Survival and Disinfectant Inactivation of the Human Immunodeficiency Virus: A Critical Review", RID 1991; 13 (May–Jun.), pp. 430–447.

Exact. excerpts from "Product Specification, Discription, Patent Application & Supporting Documentation", by EXOxEMIS, Inc., Feb. 1991.

Klebanoff et al., "Virucidal Activity of H202–generating Bacteria; Requirement for Peroxidase and Halide", Dept. of Medicine, University of Washington School of Medicine, Seattle, Washington, Sep. 24, 1973.

(List continued on next page.)

*Primary Examiner*—Mark Kopec
*Assistant Examiner*—John M Petruncio
*Attorney, Agent, or Firm*—Susanne M. Hopkins

[57] ABSTRACT

The invention relates to compositions effective for the cleansing of mammalian bones and particularly the removal of bone marrow and like blood deposits therefrom. The compositions are composed of an aqueous solution containing as its essential ingredients a detergent having a functionality of the nature of a polyoxyethylene-23-lauryl ether, a detergent having a functionality of the nature of oxyethylated alkylphenol, and water, where the compositions are free from any membrane stabilizers. The detergent having a functionality of the nature of a lauryl ether and the detergent having a functionality of the nature of oxyethylated alkylphenol are present in a weight percent ratio of about 1.65:1. Preferably the detergent having a functionality of the nature of oxyethylated alkylphenol consists of a combination of poly(ethylene glycol)-p-nonyl-phenyl-ether and otylphenol-ethyleneoxide, and the detergent having a functionality of the nature of a polyoxyethylene-23-lauryl ether, the poly(ethylene glycol)-p-nonyl-phenyl-ether and the octylphenol-ethyleneoxide are present in a weight percent ratio of about 3.3:1:1. The invention also relates to kits that comprise one or more of the compositions of the invention.

10 Claims, 14 Drawing Sheets

OTHER PUBLICATIONS

"DMIN Asceptic Tissue Demineralization", a product brochure from Osteotech, Inc. 1993.

"Cleaner, Safer Culograft Bone VIP Bone™", a product regarding VIP Bone, from Cryolife, Inc., Feb. 12, 1992.

"The Virucidal Capacity of a Surfactant/Iodophor–Based Viral Inactivation Process for Bone Allografts", a report of studies designed and funded by Cryolife, Inc., undated.

Withrow et al., "Evaluation of the Antiretroviral Effect of Various Methods of Sterilization/Preserving Cortiocancellous Bone", presented at the 36th Annual Meeting, Orthopaedic Research Society, Feb. 5–8, 1990, New Orleans, Louisianna, Transactions of the Orthopaedic Research Society, 16, 1990, pp. 226.

Garrison et al., "Comparison of Bacterial Contimation of Cadaveric Bone Allograft Collected Under Operating Room and Morgue Condition with and without the use of Decontaminating Process", presented at the Second Congress of the European Asscocation of Tissue Bank, Athena, Greece, May 1993.

Morse, "A New Surfactant/Iodophor–Based Viral Inactivation Process (VIP) for Preparation of Bone Allografts", presented at the 16th Annual Meeting of the American Association of Tissue Banks, San Diego, Aug. 1992.

"Improve Performance of Your Immunoassay Systems and Immunodiagnostics Kits", a product brochure by Medicine & Applied Sciences, Inc., undated.

"Viral Inactivation Agent for Blood Samples", an article referring to an Oct. 1990 issue of *American Clinical Laboratory* entitled an Antiviral Agent for General Use in Biological Samples.

*Virginia Tissue Bank Procedure Manual*, Section 5.9.4.5, Copyright registered on Aug. 6, 1986.

Buck et al., "Human Immunodeficiency Virus Cultured From Bone. Implications for Transplantation", Clinical Orthopaedics and Related Research, No. 251, 1990.

*Navy Tissue Bank, Tissue Bank Coordinator Manual 10. "Procurement of Deep Tissues and Bones"*, p. 9. (undated).

Shutkin, "Homologous–Serum Hepatitis following the Use of Refrigerated Bone–Bank Bone", The Journal of Bone and Joint Surgery, vol. 16–1, No. 1, 1954.

Hyatt et al., "Bone Grafting. The Procurement, Storage, and Clinical Use of Bone Homografts", The American Academy of Orthopaedic Surgeons, Ann Arbor, U.S.A., 1957.

"Transmission of HIV through Bone Transplantation: Case Report and Public Health Recommendations", Morbidity and Mortality Weekly Report, vol. 37, No. 39, 1988.

Kakaiya et al., "Tissue Transplant–Transmitted Infections", Transfusion, vol. 31, No. 3, 1991.

Tomford et al., "A Study of the Clinical Incidence of Infections in the Use of Banked Allograft Bone", The Journal of Bone and Joint Surgery, vol. 63–A, No. 2, 1981.

Furlini et al., "Antibody Response to Human Immunodeficiency Virus after Infected Bone Marrow Transplant", Eur. J. Clin, Microbiol. Infect. Dist., vol. 7, 1988.

Lord et al., "Infection in Bone Allografts. Incidence, Nature, and Treatment", The Journal of Bone and Joint Surgery, vol. 70–A, No. 3, 1988.

Bonfiglio et al., "The Immune Concept: Its Relation To Bone Transplantation", Annals New York Academy of Sciences, 1955.

Doppelt et al., "Operational and Financial Aspects of A Hospital Bone Bank", the Journal of Bone and Joint Surgery, vol. 63–A, No. 9, 1981.

Dirschi et al., "Topical Antibiotic Irrigation in the Prophylaxis of Operative Wound Infections in Orthopedic Surgery", Orthopedic Infection, vol. 22, No. 3, Jul. 1991.

Reynolds et al., "Clinical Evaluation of the Merthiolate Bone Bank and Homogenous Bone Grafts", The Journal of Bone and Joint Surgery, vol. 33–A, No. 4, 1951.

"Med Clean Mark II", a product brochure by Advanced International Marketing for a unit which includes a pressurized stream of water for bone debridement. (undated).

U.S. Department of Health and Human Services/Public Health Service, Transmission of HIV Through Bone Transplantation: Case Report and Public Health Recommendations, Morbidity and Morality Weekly Report, 37, 1988. pp. 597–599.

Mellonig, J. T. et al., "HIV Inactivation in a Bone Allograft", J. Periodontology, Dec. 1992, vol. 63, pp. 979–983.

Helenius et al., "Solubilization of Membranes by Detergents", Biochim, Biophys. Acta 415 (1975) 29–79.

COMPOSITION FOR CLEANING BONES

REFERENCE TO RELATED APPLICATION

This application is a continuation-in-part of application Ser. No. 08/395,113, filed on Feb. 27, 1995, now U.S. Pat. No. 5,556,379 which is a continuation-in-part of U.S. application Ser. No. 08/293,206, filed on Aug. 19, 1994, now abandoned the disclosures of which are incorporated herein in their entirety.

BACKGROUND OF INVENTION

1. Field of Invention

The subject invention relates to a composition for the cleansing and disinfection of bones, and cleansed bone produced thereby for use in bone grafting.

2. Discussion of Background Information

A major concern in the area of bone grafting technology is the effective and safe removal of bone marrow from the less solvent-accessible cancellous bone spaces within bone grafts.

For bone grafts, human bone may be obtained from cadaveric donors under sterile conditions in an operating suite environment of local hospitals. The bone is stored frozen until it is further processed into small grafts under similar sterile conditions, or under clean-room conditions. Procurement and processing of human tissues is typically performed by groups certified by the American Association of Tissue Banks under standard operating procedures for the processing of each specific bone graft. For instance, large bones such as the femur are thawed and debrided of excess tissue prior to being cut into smaller grafts.

Processing of small bones as well as smaller bone grafts obtained from large bones includes cleaning of bone marrow from the cancellous bone spaces using mechanical means, soaking, sonication, and/or lavage with pulsatile water flow under pressure.

Bone marrow elements include hematopoietic progenitor cells, i.e., those stem cells that will ultimately differentiate into red blood cells, white blood cells, and platelets, among others. These stem cells are rich in major histocompatibility antigens (i.e., MHC antigens) that function in immune responses. It is advantageous to have bone graft material which is essentially free of residual bone marrow, for use in the preparation of small bone grafts. Large, essentially whole, bone grafts with minimal residual bone marrow offer additional advantages in that removal of bone marrow, which may harbor potential viral particles and/or viral genomes integrated into the genomes of specific cell types present in the bone marrow, reduces the potential for transmission of infective agents such as bacteria and viruses, especially the human immunodeficiency virus (HIV), since cells capable of harboring the HIV virus are abundant in bone marrow. The removal of bone marrow from large or small bone grafts also reduces the bioburden of viruses which may be present within the bone marrow cells removed.

Conventional bone-cleaning protocols may include the use of detergents, alcohol, organic solvents or similar solutes or combination of solutes designed to facilitate solubilization of the bone marrow. Common methods may use reduced or elevated temperatures, for example, between 4° C. to 65° C.

Ethanol and detergents have been demonstrated to be bacteriocidal toward certain bacteria, such as gonorrhea, gram negative bacteria, for example, *Yersinia enterocolitica*, gram positive bacteria, for example, *Myobacterium tuberculosis* and Chlamydia, as well as acid fast bacteria. Ethanol and detergent solutions also offer advantages of enhancing solubilization of bone marrow, reducing surface tension properties of aqueous solutions, and inactivating viruses and bacteria.

Detergents are amphiphile compounds which facilitate solubilization of relatively insoluble lipids present in, for example, bone marrow, yet at high concentrations tend to form micellar structures Helenius, A. and Simons, K., "Solubilization of Membranes by Detergents," *Biochim. Biophys. Acta* 415:29–79 (1975). The formation of micellar structures tends to limit the effective concentration range for detergent solutions, and thus, soaking of bone in a given volume of detergent solution may not be totally effective in that the absolute amount of detergent present is limited and if the amount of lipid material to be solubilized exceeds the solubilization capability of the detergent present, lipid solubilization will not be complete. By continually changing the detergent solution over time, it becomes possible to completely solubilize all solubilizable lipid present in bone graft.

Typically, hydrogen peroxide is used to oxidize the colored elements within the bone marrow, which results in a cleaner appearance. However, such bone often still contains bone marrow which is extremely immunogenic.

Further, most bone grafts are currently stored in the freeze-dried state. Freeze-drying removes water from the grafts, but lipid elements present in the membranes of the bone marrow cells and in vesicles present in adipocytes (i.e., fat storage cells) typically leak from the grafts after being placed in their final storage and distribution containers. These residues often give the appearance that the graft itself is not clean.

In fact, with conventional bone-cleaning protocols the graft often harbors bacteria, viruses and/or fungi in the bone marrow.

Cleaning of bone marrow from small bone grafts (for example, tarsels and meta tarsels as small as 1–5 cm) has been described in the scientific literature and in brochures and documents made public by groups involved in the procurement and processing of human tissues. A for-profit public corporation, Cryolife, Inc. (Marietta, Ga.) promotes a bone cleaning process designated as VIP™ (Viral Inactivation Process) and claims that the process provides "Cleaner bone through mechanical removal of debris and tissue such as bone marrow, lipids and blood components" and "Safer bone through inactivation of pathogens such as HBV and HIV (greater than 5-log kill) as well as bacteria and fungi" (Cryolife Orthopedics, Inc., brochure 12, February, 1992; Cryolife literature directed to Organ and Tissue Procurement Program Directors dated Feb. 20, 1992).

Minimal information regarding the methods of the process is available but it is described as a multi-step approach having three phases:1) preliminary surface disinfection of procured tissue for the protection of processing technicians during thawing, debriding and cutting; 2) cleaning and removal of debris from the cut pieces with a surfactant at elevated temperature; and 3) terminal disinfection of the cleaned bone grafts ( The Viricidal Capacity of a Surfactant/Iodophor-Based Viral Inactivation Process for Bone Allografts, Cryolife documentation). The VIP process is claimed to both clean bone allografts, e.g., a femur head, and to inactivate a variety of bacteria and viruses without affecting bone strength or biological properties. However, according to documents made public by Cryolife, Inc., the process is used to clean the surfaces of large bone grafts and to remove bone marrow from the cancellous bone spaces of small bone grafts cut from the larger grafts.

A second, for-profit publicly held corporation, Osteotech, Inc., Shrewbury, N.J., describes a bone graft cleaning process called Permein ("a combination of ethanol and non-ionic detergent"; Mellonig, J. T., Prewett, A. B., and Moyer, M. P., *J. Periodontal* 63:979–983 (December, 1992). This Process involves the use of a solution of ethanol and detergent to clean bone grafts. Details of the process and detergents utilized are not currently available. Bone is soaked in the solution and it is claimed that the combination of ethanol and detergent facilitates permeation of the solution into bone. The process has been demonstrated to clean small cut-bone grafts and to be capable of inactivating the HIV in bone allograft (finely ground bone) (Mellonig, Prewett, and Moyer, *J. Periodontology:*979–983 (December, 1992).

SUMMARY OF INVENTION

The invention addresses the deficiencies and problems in the prior art by novel compositions which contains a protein solubizing detergent and a lipid solubilizing detergent, which are quite effective in removing bone marrow from bones and bone grafts. The detergents are effective in the formation of micelles containing bone marrow particles and/or debris. The concentration of the detergents is such that the bone marrow particles and/or debris are (1) completely solubilized and (2) kept in solution. In this fashion, the concentration of the particles and/or debris is reduced to below the critical micelle concentration value (CMC). (Critical micelle concentration is a fixed number, and values are assigned to detergents based on their respective detergent properties and the molecular weights at which they function as detergents.) Thus, the particles and/or debris are in monomeric form so as to be easily washed out of the bone graft.

The compositions of the invention comprise a superior, safe, non-toxic, non-pyrogenic solvent and detergent based aqueous agent that effectively solubilizes and removes bone marrow from bone. The invention penetrates the less solvent accessible cancellous spaces within the bone grafts, thus providing effective removal of bone marrow in one easy and quick cleansing step. Bone grafts cleaned with the inventive composition retain bone inductive properties while the bone marrow debris is quickly solubilized and removed. Bone marrow removal reduces the bioburden of viruses, bacteria and fungi which grow and may be present in the bone marrow.

In addition, the compositions of the invention are easily removed by a simple washing procedure, and virtually no residual detergents are present in the bone after washing. The compositions of the invention are an improvement over the art in providing easy-to-use excellent cleaning power at a low cost.

Well balanced optimized low concentrations of anionic and non-ionic surfactants and detergents of the invention act synergistically to lyse, solubilize and keep in solution proteins, lipids, hemopoietic progenitor cells, red blood cells, white blood cells, platelets and histocompatible antigens. The surfactants preferably include Nonoxynol-9, (a known anti HIV agent), Brij-35 (protein solvent), Tergitol NP-40 (a lipid solvent) and IGEPAL CA 630. These surfactants are provided as micelles in optimized critical micelle concentrations (CMC) to dissolve bone marrow particles and/or debris, which after being consumed in the cleansing process, are reduced to a concentration below the CMC value. At that concentration level, the particles and/or debris are in monomeric form (i.e., act as monomers), and can subsequently be easily removed via washing steps, leaving no detectable residues in the bone.

Accordingly, objects of the invention include the development of compositions which are effective for the cleaning and disinfecting of bones, such as by facilitating the removal of bone marrow and other blood deposits from the interstitial lumen and cancellous bone space.

Another object of the present invention is to provide a bone cleaning composition which removes most or substantially all of the bone marrow elements from bone grafts with minimal handling and processing, to reduce the risk of viral, bacterial and fungal transmission.

It is a further object of the invention to provide a composition which improves solvent penetration into and through the bone and increases the solubility of bone marrow, facilitating its removal from the bone.

These and other objectives of the instant invention have been realized by use of an aqueous composition which contains as its essential ingredients a protein solubilizing detergent a lipid solubilizing detergent and water. The protein solubilizing detergent and the lipid solubilizing detergent should preferably be present in a weight percent ratio of about 1:2, respectively.

Preferably, the lipid solubilizing detergent consists of a combination of two compounds selected from the group consisting of poly(ethylene glycol)-p-nonyl-phenyl-ether, octylphenol-ethyleneoxide, polyoxyethylene alcohols, polyethylene glycol pisooctylphenylethers, polyoxyethylene nonylphenol, and polyoxyethylene sorbitol esters. Poly (ethylene glycol)-p-nonyl-phenyl-ether and octylphenol-ethyleneoxide are the preferred two compounds. The protein solvent and the two compounds are preferably present in a weight percent ratio of about 3:1:1, respectively.

In one embodiment, the invention relates to bone cleansing compositions containing as essential components i) between about 0.001 to about 2 weight percent (more preferably from about 0.01 to about 0.5 weight percent and most preferably, about 0.066 weight percent) of a protein solubilizing detergent (such as lauryl ether, preferably polyoxyethylene-4-lauryl ether, and more preferably one of the Brij series), ii) between about 0.001 and about 2 weight percent (more preferably from about 0.01 to about 0.5 weight percent and most preferably about 0.04 weight percent) of a lipid solubilizing detergent, (such as oxyethylated alkylphenol, preferably poly(ethylene glycol)-p-nonyl-phenyl-ether and/or octylphenol-ethyleneoxide, and more preferably Nonoxynol 9 and/or Tergitol NP-40, and/or IGEPAL CA 630), and iii) water preferably endotoxin-free deionized/distilled water).

Preferably, the lipid solubilizing agent consists of a combination of two compounds selected from the above-referenced group. The two compounds are preferably each present in about 0.02 wt. %.

In a preferred embodiment, the invention relates to bone cleansers composed of an aqueous solution containing as its essential ingredients i) about 0.066 wt. % polyoxyethylene-4-lauryl ether, ii) about 0.02 wt. % poly(ethylene glycol)-p -nonyl-phenyl-ether (such as, preferably, Nonoxynol 9), iii) about 0.02 wt. % octylphenol-ethyleneoxide (such as, preferably, Tergitol NP-40) or IGEPAL CA 630; and iv) water (preferably, endotoxin-free deionized/distilled water).

In another embodiment, the invention also relates to a kit for cleaning a bone for a bone graft, comprising a solution containing one or more of the above-described compositions. The kit may optionally include instructions such as instructions for dilutions necessary to obtain appropriate weight percentages of the components in an aqueous solution.

BRIEF DESCRIPTION OF THE FIGURES

FIG. 1. This figure illustrates growth of human dermal fibroblasts in alpha-modified Minimum Essential Medium supplemented with 10% fetal calf serum with and without treatment in a minimal volume of Dulbecco's Phosphate Buffered Saline (DPBS). Treatment with the solution used to carry test reagents in subsequent studies does not alter the proliferation potential of the test cell line.

FIG. 2. This figure illustrates the potential for detergents present in ALLOWASH™ solution to bind to the tissue culture flask such that its effective concentration(s) might be altered under the present experimental conditions. Flasks were treated for 48 hours with 0.02× AL in DPBS, washed with tissue culture medium and cells seeded and grown to confluency. AL does not bind to the tissue culture flasks since the concentrations of AL used would be toxic to the cells if AL were carried over into the tissue culture medium.

FIG. 3. This figure illustrates the potential for fetal calf serum (as a representative protein solution such as might be present in solubilized bone marrow) to bind detergents present in ALLOWASH™ solution, reducing their effective concentrations. Two concentrations of fetal calf serum are tested (10% and 34%) with and without 0.01× ALLOWASH™ solution. The presence of high concentrations of protein in the tissue culture medium do not alter the toxicity (cell lysis) of this concentration of AL to representative mammalian cells.

FIG. 4. This figure illustrates the results of experiments where human dermal fibroblasts were treated with 0.11× AL for 36 hours and then washed free of AL and cultured in tissue culture medium. Cell numbers were determined as an assessment of proliferative viability of treated versus non-treated cells. The 0.01× concentration of AL virtually eliminated all proliferative potential of the human dermal fibroblast cells.

FIG. 5. This figure illustrates the results of experiments where human dermal fibroblasts were treated with 0.005× AL for 36 hours and then washed free of AL and cultured in tissue culture medium. Cell numbers were determined as an assessment of proliferative viability of treated versus non-treated cells. The 0.005× concentration of AL was less "toxic" to the human dermal fibroblasts than 0.01× AL, but significantly reduced the proliferative viability of the cells.

FIG. 6. This figure illustrates the results of experiments where human dermal fibroblasts were treated with 0.001× AL for 36 hours and then washed free of AL and cultured in tissue culture medium. Cell numbers were determined as an assessment of proliferative viability of treated versus non-treated cells. The 0.001× concentration of AL did not alter the proliferative viability of the human dermal fibroblast cells.

FIG. 7. This figure illustrates the results of experiments where human dermal fibroblasts were treated with 0.0005× AL for 36 hours and then washed free of AL and cultured in tissue culture medium. Cell numbers were determined as an assessment of proliferative viability of treated versus non-treated cells. The 0.0005× concentration of AL did not alter the proliferative viability of the human dermal fibroblast cells.

FIG. 8. This figure illustrates three replicate assays to determine the critical micelle concentration (CMC) of Nonidet P-40. Optical density of NP-40 solubilized dye as a function of concentration of NP-40 is plotted such that the CMC value can be determined as the intersect point of two regression lines drawn through the data points. The calculated CMC values in each data plot are 0.23 mM, 0.23 mM, and 0.24 mM in plots A, B and C, respectively.

FIG. 9. This figure illustrates three replicate assays to determine the critical micelle concentration (CMC) of Brij-35. Optical density of Brij-35 solubilized dye as a function of concentration of Brij-35 is plotted such that the CMC value can be determined as the interest point of two regression lines drawn through the data points. The calculated CMC values in each data plot are 0.09 mM, 0.132 mM, and 0.138 mM in plots A, B and C, respectively.

FIG. 10. This figure illustrates three replicate assays to determine the critical micelle concentration (CMC) of Nonoxynol-9 ( Non-9). Optical density of Non-9 solubilized dye as a function of concentration of Non-9 is plotted such that the CMC value can be determined as the intersect point of two regression lines drawn through the data points. The calculated CMC values in each data plot are 0.06 mM, 0.055 mM, and 0.07 mM in plots A, B and C, respectively.

FIG. 11. Transectional cut of a noncleaned proximal femur showing the presence of bone marrow in both the intramedullary canal and cancellous bone space.

FIG. 12. Transectional cut of a proximal femur cleaned with ALLOWASH™ solution showing the absence of bone marrow in both the intramedullary canal and cancerous bone space and by reference the ability of the ALLLOWASH™ solution to solubilize the bone marrow present in bones.

FIG. 13. Scanning electron photomicrograph of cancellous bone obtained from a noncleaned proximal femur showing the presence of bone marrow in the cancellous bone space.

FIG. 14. Scanning electron photomicrograph of cancellous bone obtained from a proximal femur cleaned ALLOWASH™ solution showing the absence of bone marrow in the cancerous bone space. The scaffold-like structures visible in the photograph illustrates trabecular bone which forms the bone portion of cancellous bone space.

DETAILED DESCRIPTION OF THE PREFERRED EMBODIMENTS

Figure 1:
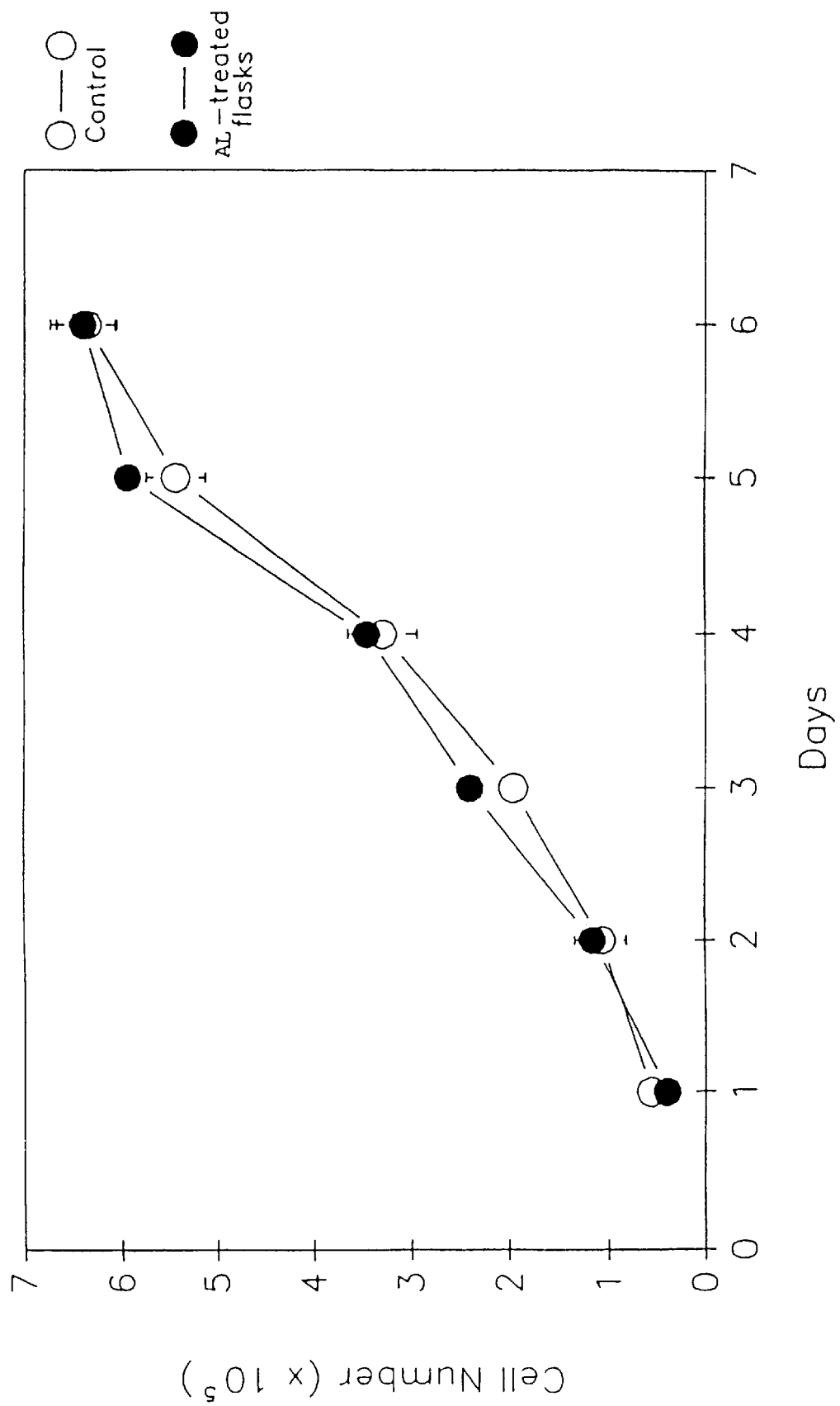
In FIGS. 1–14, "AL" stands for ALLOWASH™ Solution.
Figure 2:
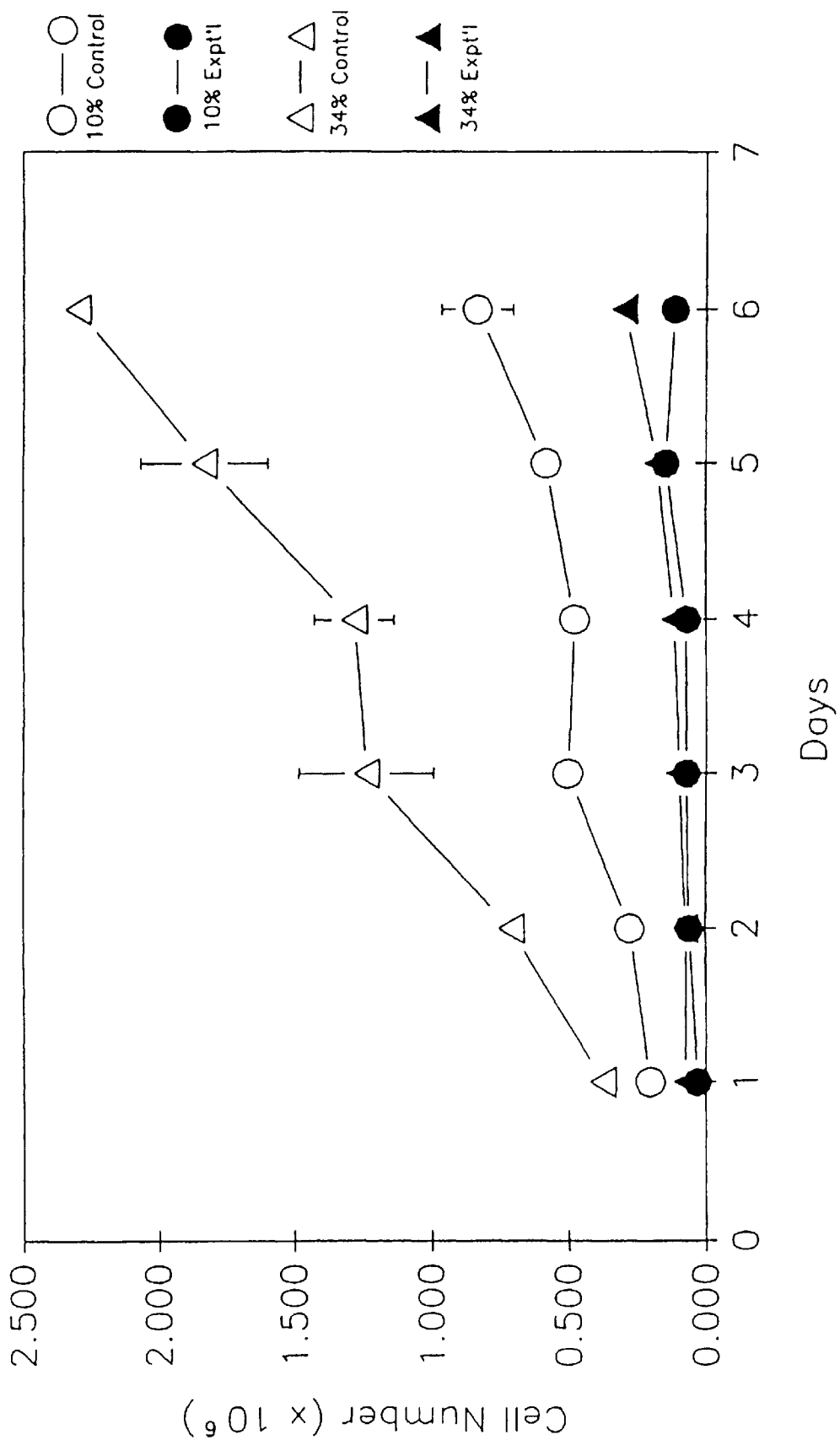
Figure 3:
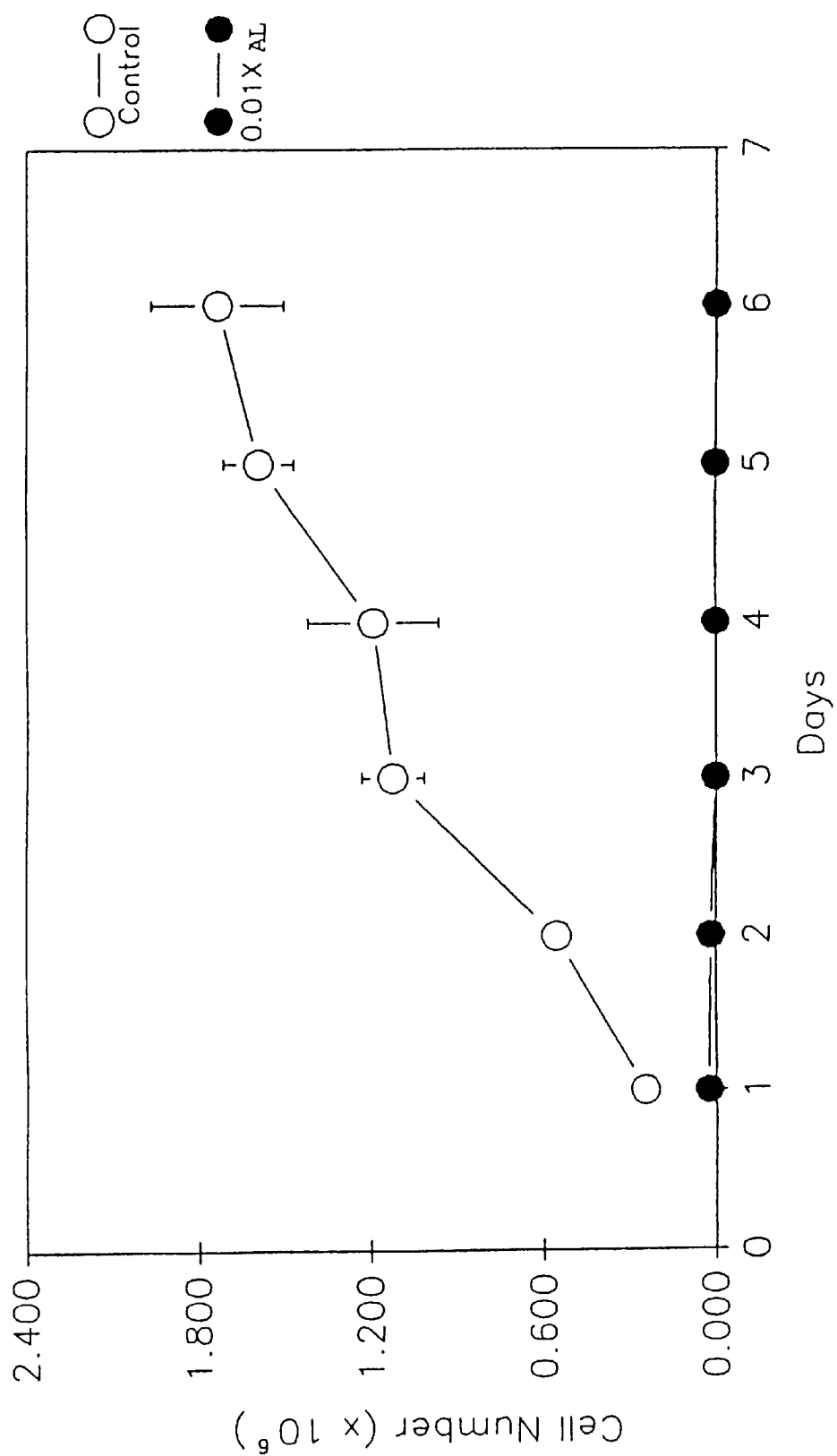
Figure 4:
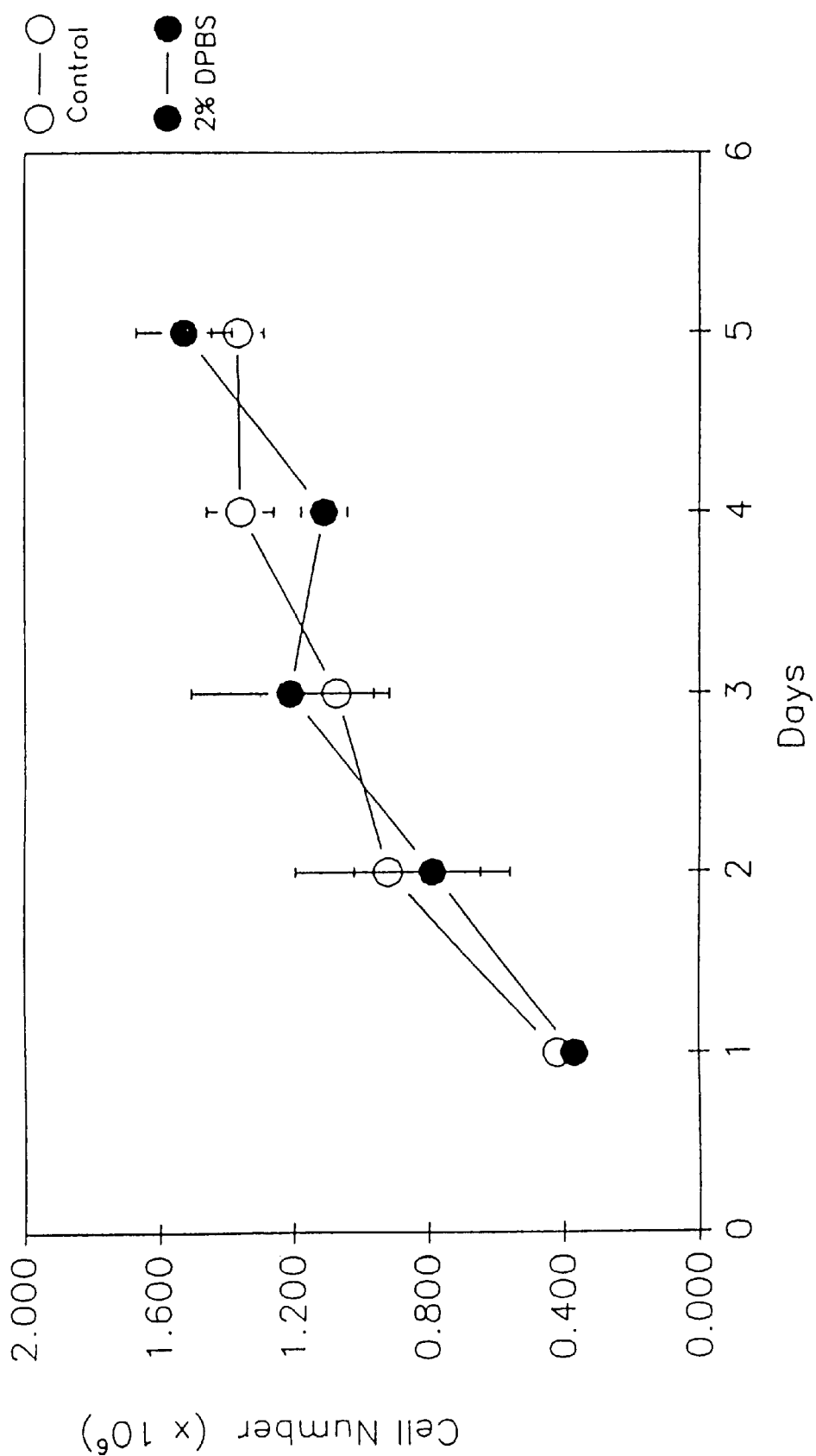
Figure 5:
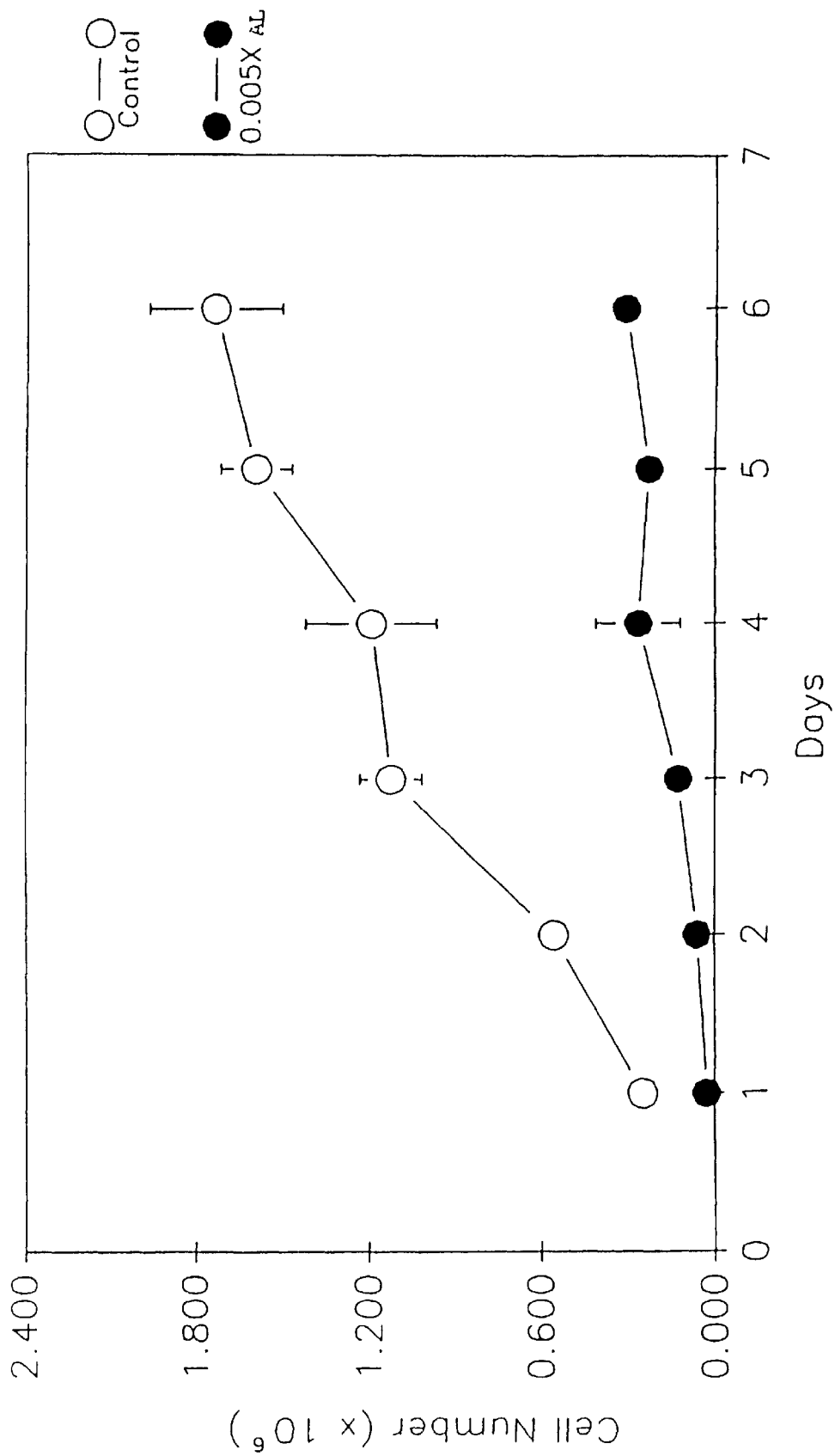
Figure 6:
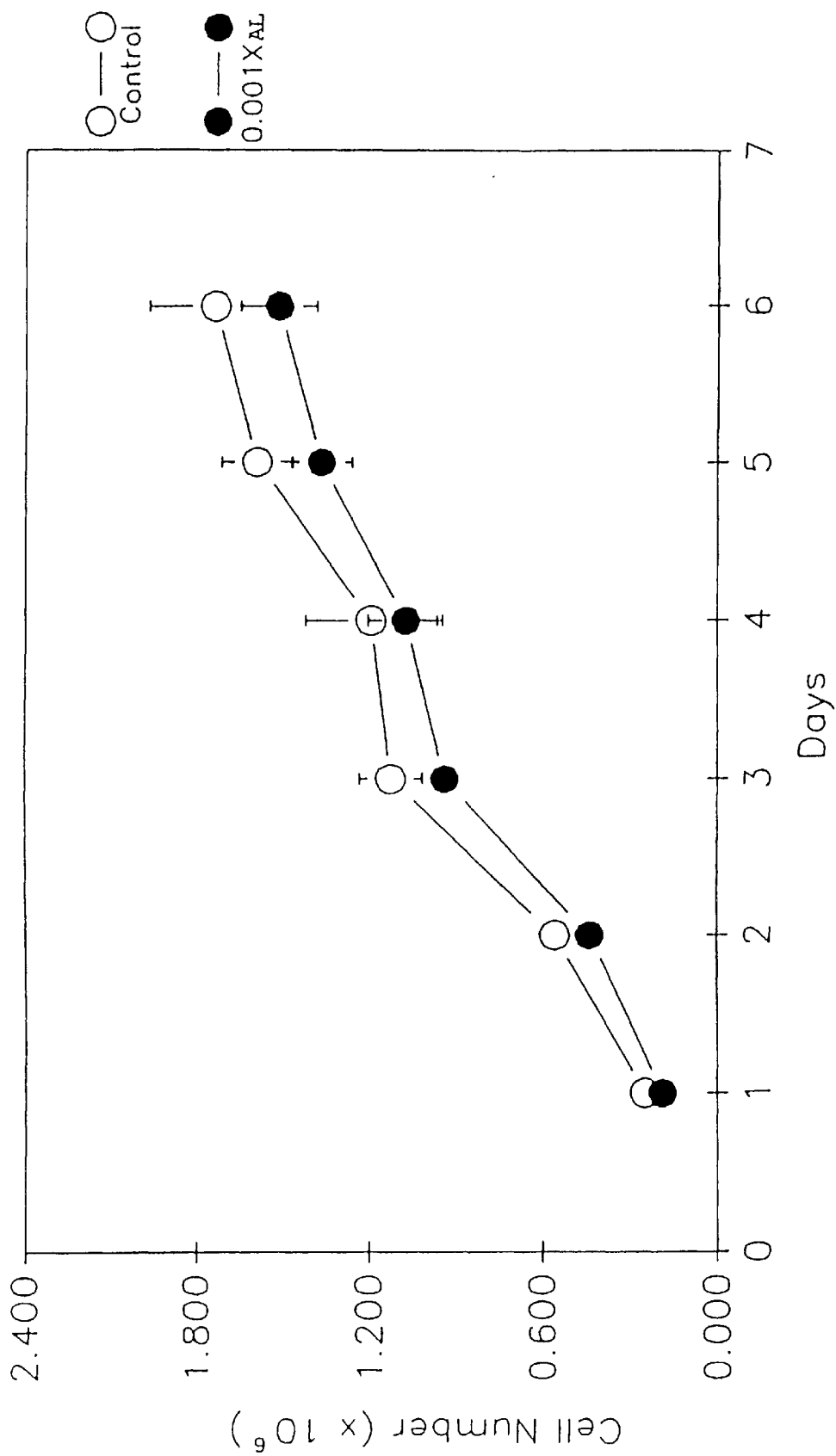
Figure 7:
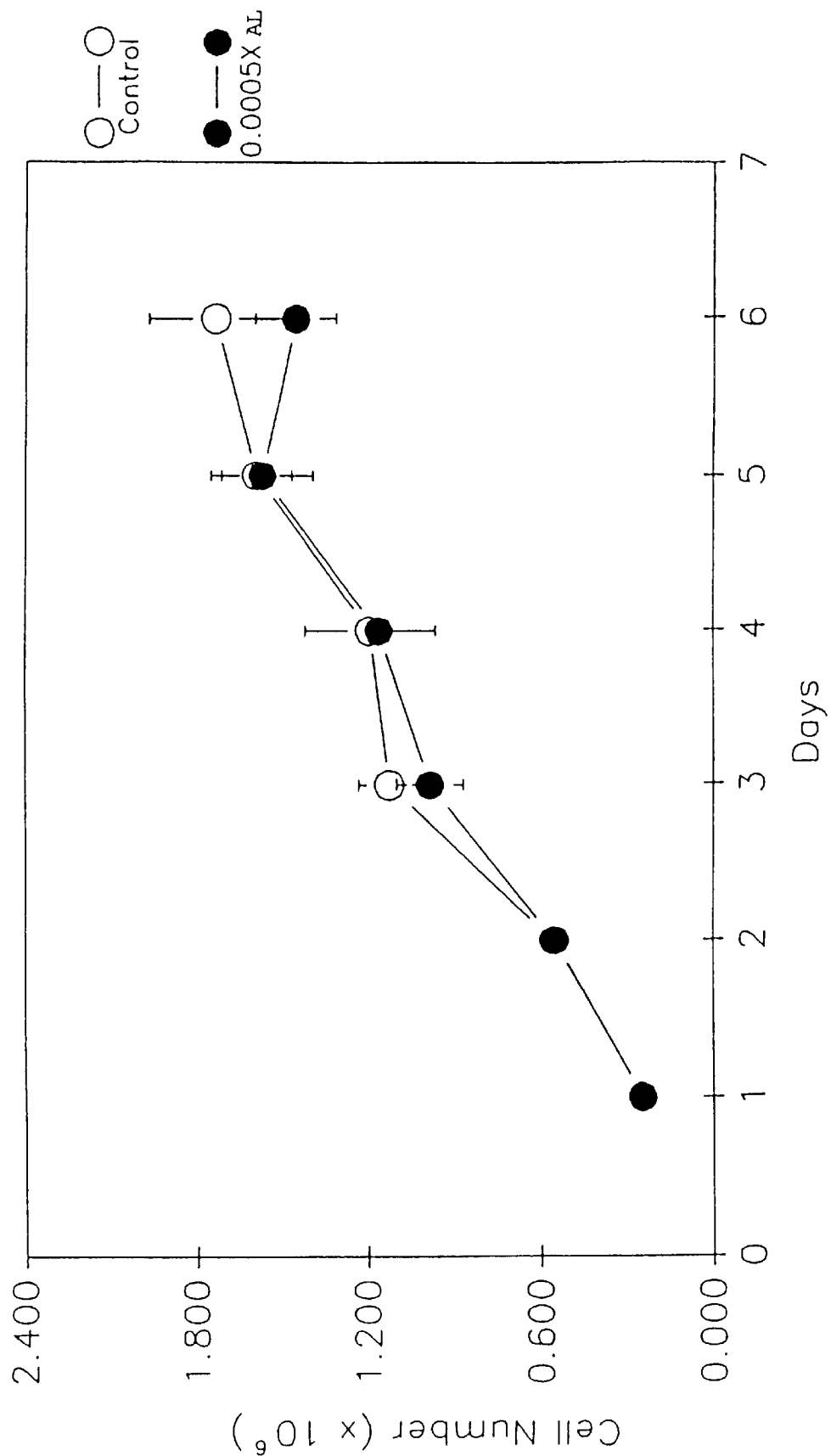
Figure 8A:
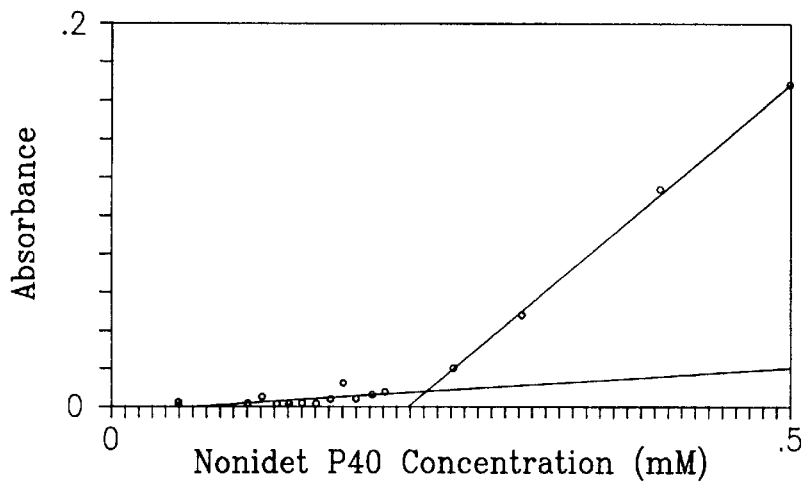
Figure 8B:
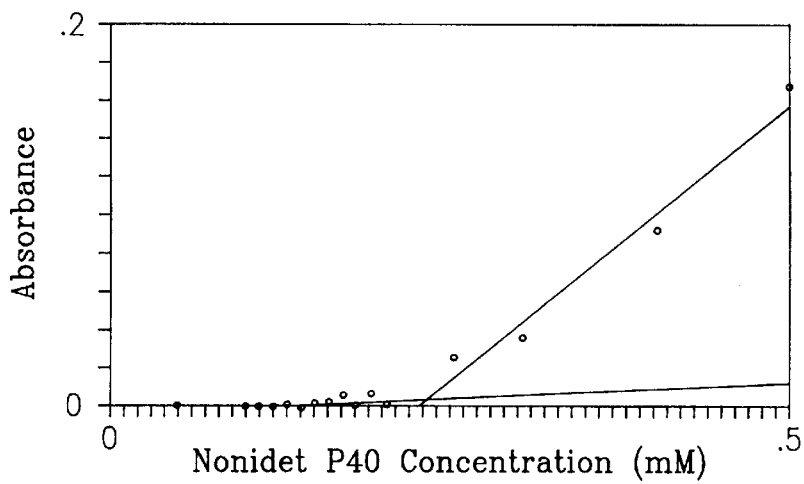
Figure 8C:
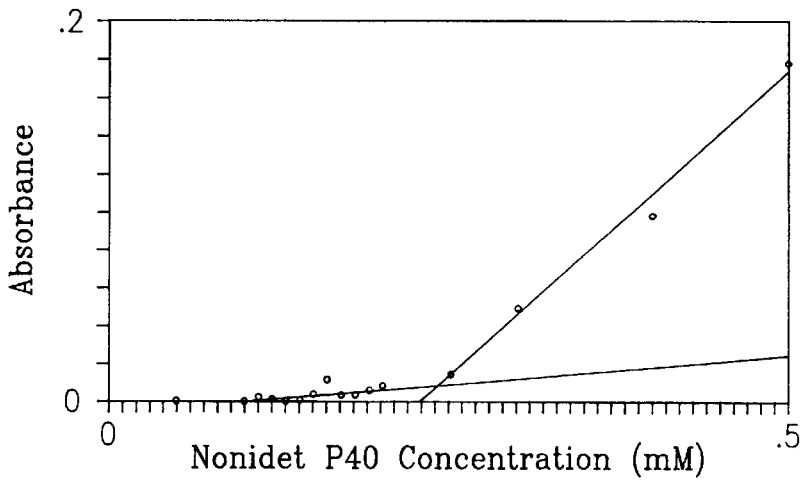
Figure 9A:
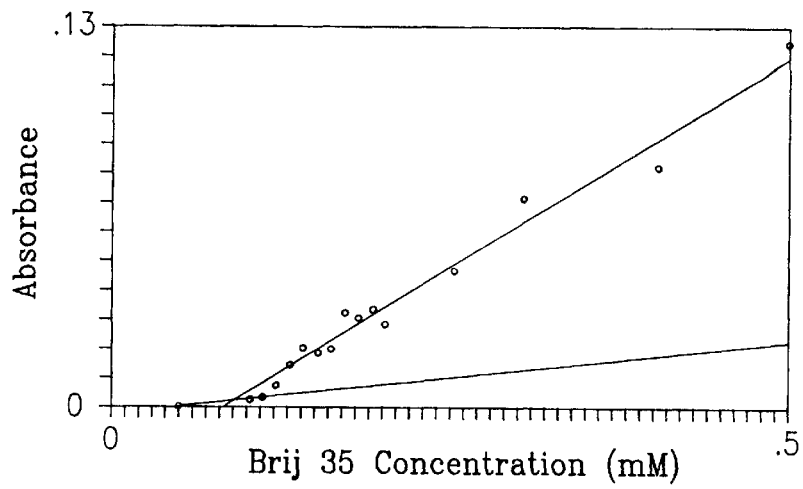
Figure 9B:
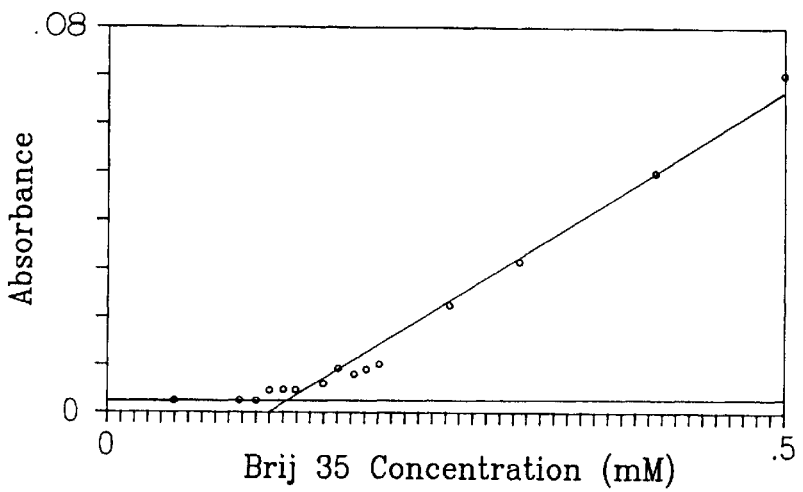
Figure 9C:
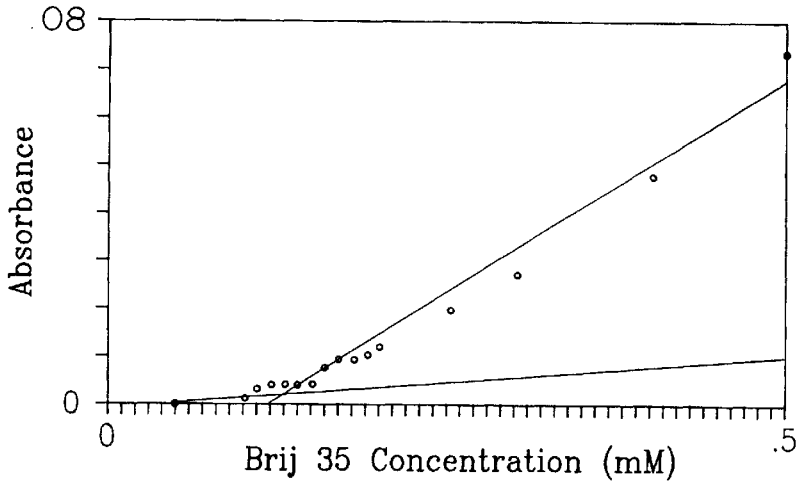
Figure 10A:
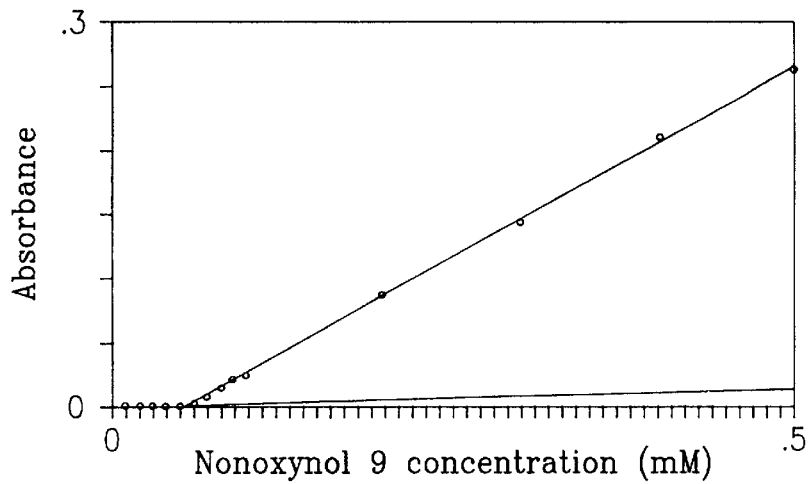
Figure 10B:
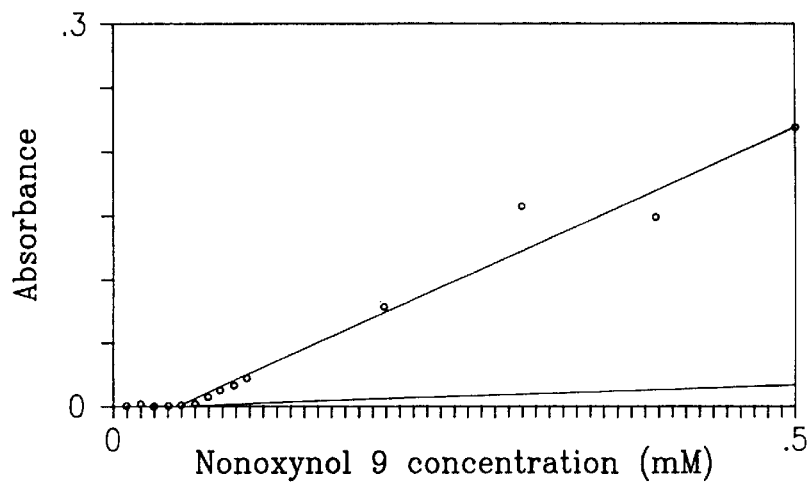
Figure 10C:
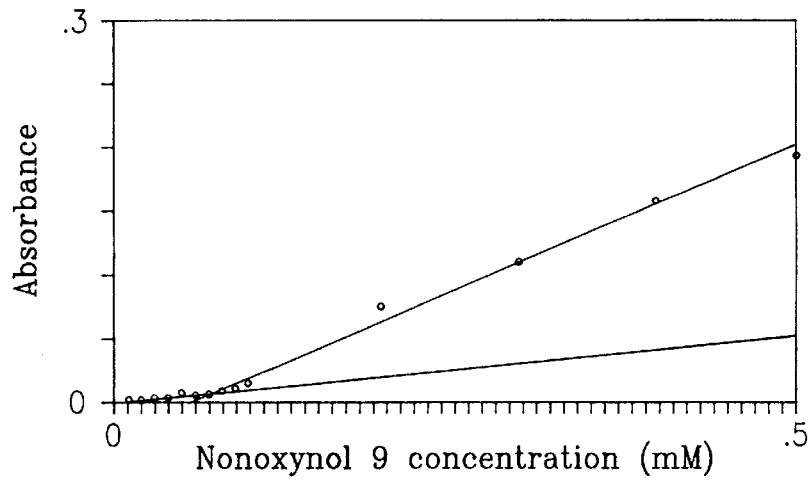
Figure 11:
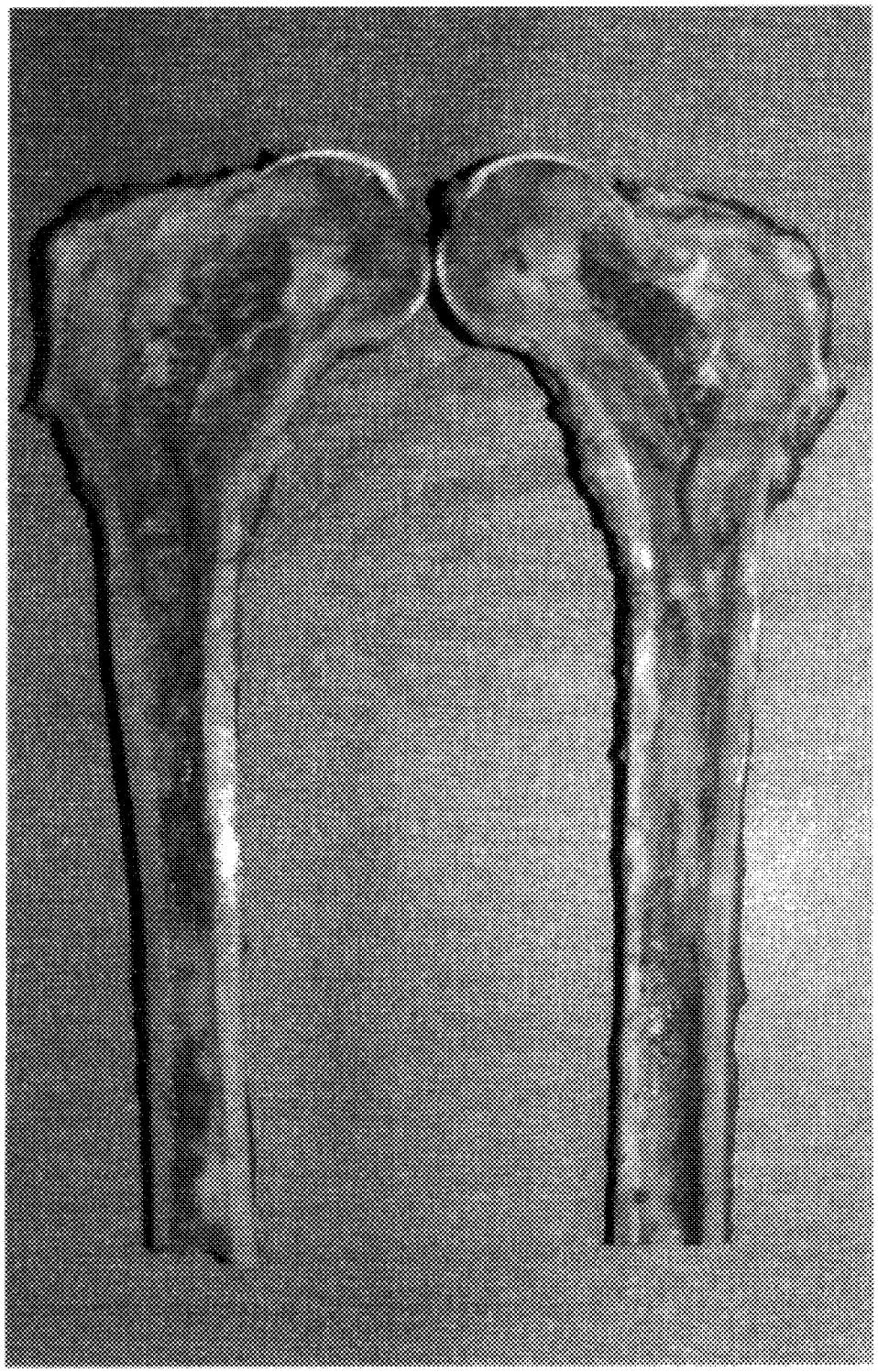
Figure 12:
Figure 13:
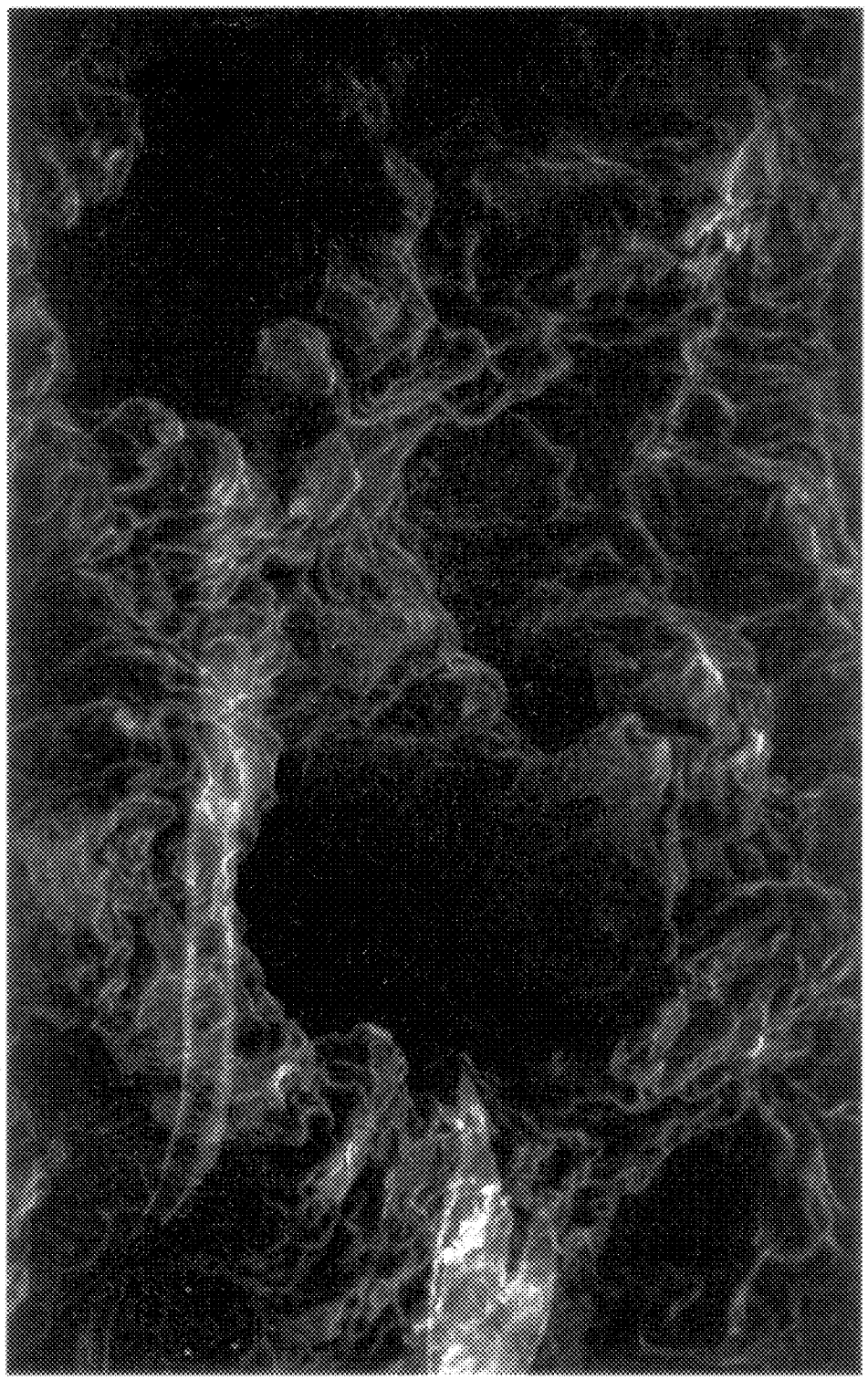
Figure 14:
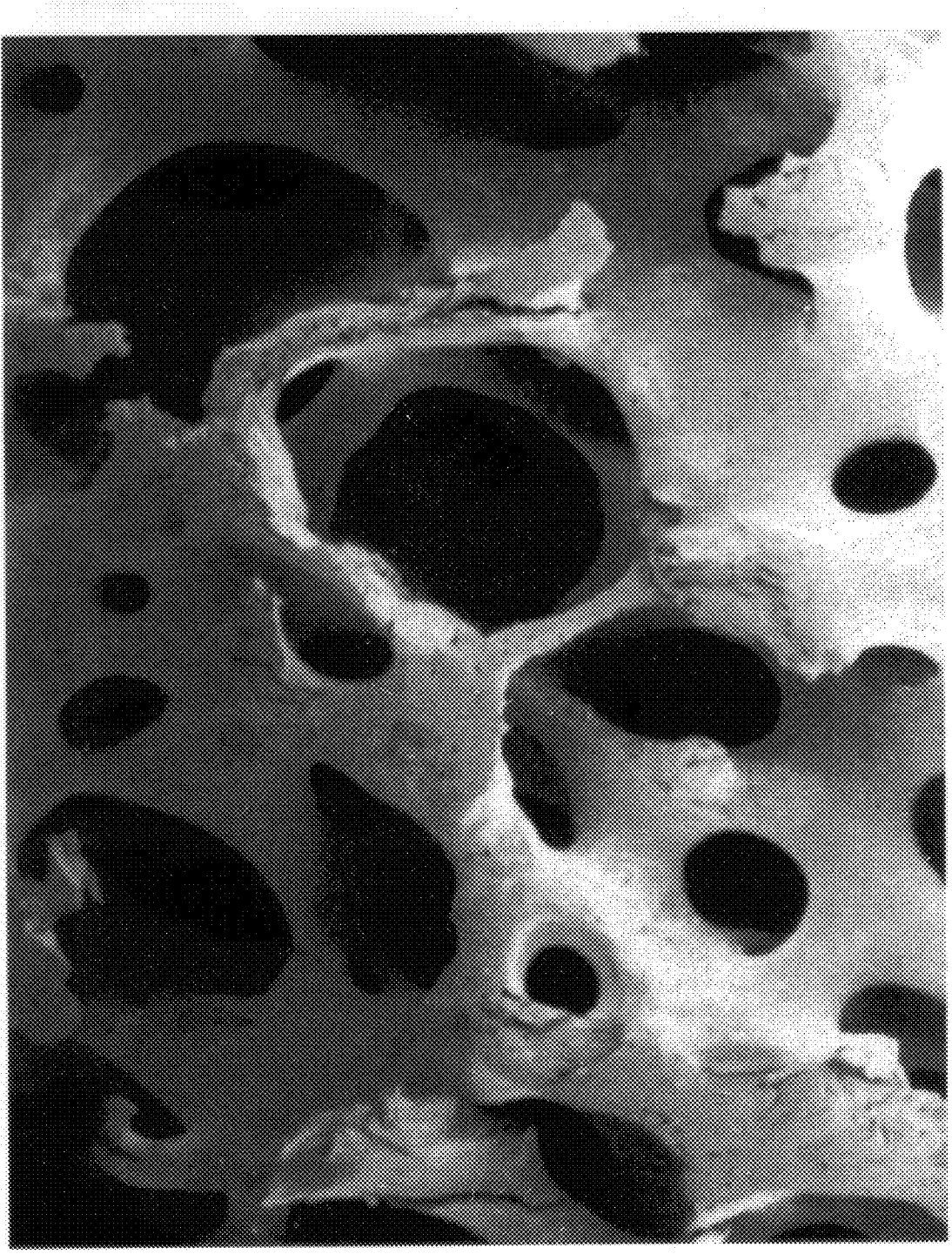

The bone cleaning compositions according to the present invention result in the effective removal of substantially all of the bone marrow elements within the cancellous bone spaces of bone grafts. The bone cleaning composition is effective to remove most or substantially all of the bone marrow elements from large and small bone grafts with minimal handling and processing, while reducing the risk of viral, bacterial and fungal transmission.

The components of the invention should be non-toxic and/or leave a non-toxic residual concentration of materials in the bone after flushing with the second solution. In particular, following cleaning of bone grafts, it is necessary that residual detergents or other components which may remain associated with the bone graft are not toxic towards human fibroblast cells expected to migrate into the bone graft material(s) following implantation.

As explained above, in order that the composition be effective for the cleansing of bones, and in the removal of bone marrow and like blood deposits, the composition should be composed of an aqueous solution containing as its essential ingredients water (such as, preferably, endotoxin-free deionized/distilled water), and at least two detergents: a protein solubilizing detergent and a lipid solvent detergent.

The protein solubilizing detergent should be present at between about 0.001 to about 2 weight percent, more preferably from about 0.01 to about 0.5 weight percent, and most preferably about 0.066 weight percent. The lipid solubilizing agent should be present at between about 0.001 to about 2 weight percent, more preferably from about 0.01 to about 0.5 weight percent, and most preferably about 0.04 weight percent. In other words, the lipid solubilizing agent and the protein solubilizing agent are present in a weight percent ratio of about 1.65:1, respectively.

The protein solubilizing agent may be a lauryl ether, which may be selected from the group consisting of polyoxyethylene-23-lauryl ether (such as Brij series, Lubrol W, etc.), polyoxyethylene (9) lauryl ether (such as $C_{12}E_{18}$), polyoxyethylene (9) lauryl ether (such as $C_{12}E_9$), dodecyl-maltoside lauryl maltoside (such as Dodecyl beta-D-maltopyramoside), decaoxyethylene monolauryl ether (such as GENEPOL C-100), octaethylene glycolisotridecyl ether (such as GENAPOL X-080), polyoxyethylene (8) isotridecyl ether (such as GENAPOL X-080), polyoxyethylene (10) isotridecyl ether (such as GENAPOL X-100), PEG (10) tridecyl ether (such as GENAPOL X-100), sodium lauryl sulfate, and sodium dodecyl sulfate.

The protein solubilizing agent includes Brij 35, which is the equivalent of a 35% solution of polyoxyethylene-4-lauryl ether. In such a case, the weight percent of Brij 35 in the composition of the invention should be adjusted so that the final weight percent ratio is 0.066 wt. % Brij 35:0.04 wt. % oxyethylated alkylphenol-functioning component. This is further explained in the examples below.

The lipid solubilizing agent may be oxyethylated alkylphenol, which may be selected from the group of consisting of poly(ethylene glycol)-p-nonyl-phenyl-ether, octylphenol-ethyleneoxide, polyoxyethylenealcohols, polyethyleneglycol pisooctylphenylethers (such as Triton X series), polyoxyethylene esters, 1-argitol, polyoxyethylene nonylphenol, and polyoxyethylene sorbitol esters (such as Tween series and Emasol series).

It is preferable that the lipid solubilizing agent consists of two compounds selected from the group consisting of poly (ethylene glycol)-p-nonyl-phenyl-ether, octylphenol-ethyleneoxide, and polyoxyethylene alcohols, polyethylene glycol p-isooctylphenylethers, polyoxyethylene nonylphenol, and polyoxyethylene sorbitol esters. More preferably, the compounds are poly(ethylene glycol)-p-nonyl-phenyl-ether and octylphenol-ethyleneoxide. Preferably, the two compounds are each present in 0.020 wt. %.

That is, the protein solubilizing agent and the two compounds are preferably present in a weight per cent ratio of about 3.3:1:1, respectively.

In a preferred embodiment, the solution comprises ALLOWASH™ solution, available from LifeNet Research Foundation, 5809 Ward Court, Virginia Beach, Va. 23455, ALLOWASH™ solution contains three detergents, i.e., (1) Brij-35 (more specifically, polyoxyethylene-r-lauryl ether having the chemical formula $C_9H_{19}(OCH_2CH_2)_4OH$), (2) Tergitol NP-40 (sometimes known as Nonidet P-40 or NP-40) having the chemical name octylphenol-ethyleneoxide, or IGEPAL® CA 630, and (3) Nonoxynol-9 having the chemical name poly(ethylene glycol)-p-nonyl-phenyl-ether, or IGEPAL® CA 630.

Polyoxyethylene-4-lauryl ether is useful in that it acts as a protein solubilizing detergent and is used extensively in electrophoreses of proteins where additional charge problems might affect separation. Thus, in the cleaning solutions of the invention, polyoxyethylene-4-lauryl ether is believed to serve in enhancing solubility of the bulk proteins in the bone marrow, keeping them "in solution" once solubilized.

Octylphenol-ethyleneoxide and poly(ethylene glycol)-p-nonyl-phenyl-ether are useful in solubilizing membranes from cell (plasma) membranes. Thus, in the cleaning solutions of the invention, octylphenol-ethyleneoxide and poly (ethylene glycol)-p-nonyl-phenyl-ether are believed to serve primarily in literally solubilizing the plasma membranes of the bone marrow cells.

It is important in this invention that at least one of the detergents be present in a concentration above its critical micelle concentration. Detergents are typically evaluated based on their "critical micelle concentration" (CMC). The CMC is that concentration of detergent in solution where free molecules or detergent begin to aggregate into micellar structures. In the cleaning compositions of the invention, the concentration of at least one of the detergent components should exceed its CMC so that there is sufficient detergent available in the solution to have micelles present in the solution to replenish monomeric detergent as it is consumed in bone marrow solubilization. Notably, however, the invention is still effective in cleaning bones if the concentration of one or two of the detergents (especially octylphenol-ethyleneoxide or Tergitol NP-40) drops below its CMC. For example, if the cleaning solution becomes diluted.

For Brij-35, the published CMC is approximately 0.092 mM (millimolar) and was experimentally determined (by detergent mediated solubilization of an "insoluble" dye) to be about 0.09 mM+/−0.026 mM; for Nonoxynol 9, the published CMC is approximately 0.0812 mM and was experimentally determined to be about 0.062+/−0.008 mM; and for Nonidet P-40, the published CMC is approximately 0.11 to 0.29 mM and was experimentally determined to be about 0.234+/−0.005 mM. For this invention, the higher CMC values reflect greater effectiveness in cleaning bone grafts, because after the bone marrow particles and/or debris are "consumed" into micelles their concentration falls below the CMC values and they are in soluble monomeric form.

The bone cleaning solution can comprise about 0.0001× to 10× concentration, of a 1× concentration detergent solution containing about 0.066 weight percent polyoxyethylene-4-lauryl ether (about 0.066 weight percent Brij-35), about 0.020 weight percent Tergitol NP-40, and about 0.020 weight percent Nonoxynol-9 in endotoxin free water (such as ALLOWASH™ solution, where Brij-35 is preferably used). Preferably, the solution comprises about 0.001× to 0.1× concentration of the 1× concentration detergent solution, and more preferably, about 0.001× to 0.01× concentration of the 1× concentration detergent solution, and most preferably, about 0.005× to 0.01× of the 1× concentration detergent solution.

A 0.01× concentration of the ALLOWASH™ solution comprises a solution of 1 ml of the 1× concentration solution in 99 ml of endotoxin free water, and other solutions comprise corresponding dilutions and/or concentrations thereof. At a 0.01× concentration of ALLOWASH™ solution, all three detergents are above their critical micelle concentrations (Brij-35 concentration is 0.55 mM, Non-9 concentration is 0.32 mM, and NP-40 concentration is 0.33 mM).

For example, a 0.01× concentration solution comprises a solution of 1 ml of the 1× concentration solution in 99 ml of endotoxin free water to provide a solution comprising 0.00066 weight percent Brij-35, about 0.0002 weight percent Nonidet P-40, and about 0.0002 weight percent Nonoxynol-9 in endotoxin free water, and a 10× concentration solution comprises 0.66 weight percent Brij-35, about 0.2 weight percent Nonidet P-40, and about 0.2 weight percent Nonoxynol-9 in endotoxin free water.

Formulations including solutions of detergents of Brij 35, Nonidet P-40, and Nonoxynol-9 are disclosed in U.S. patent application Ser. No. 08/395,113, now U.S. Pat. No. 5,556,379 filed Feb. 27, 1995. U.S. patent application Ser. No. 07/696,955 abandoned discloses these detergents in combination with membrane stabilizers. Both foregoing applications are hereby incorporated by reference especially for their disclosure concerning detergents that are effective in reducing or killing microorganisms and viruses in a relatively short period of time.

In accordance with the present invention, the bone cleaning compositions can comprise concentrations of about 0.0001× to 10×, preferably 0.001× to 0.1×, more preferably 0.001× to 0.01×, and most preferably 0.005× to 0.01×. As discussed above, these solutions should preferably be at a concentration so that upon completion of cleaning of the bone, e.g., prior to implantation, the concentration of detergents and/or any of materials in the concentration solution is below a toxic level. For example, a 0.01× concentration solution is a preferred solution, because removal of 90 percent of this solution from the bone, such as by subsequent flushing with secondary solutions, reduces the concentration to approximately a 0.001× solution, which is the non-toxic level. Thus, a 0.01× solution provides a highly cost effective solution having an effective concentration of detergents without wasting excess detergents.

Optionally, the solution may include alcohols, such as ethanol. Alcohols are advantageous in that they improve the action of the cleaning solution of the invention as a bone marrow solubilizing agent. For instance, ethanol, when included, is included in a solution of about 5 to 95% ethanol, measured by a volume-to-volume ratio, and more preferably in the range of about 10 to 30% ethanol, measured by a volume-to-volume ratio.

The cleaning solutions of the present invention can include any extraneous components in amounts that are not detrimental to the cleaning of the bone. For example, components that may be a detrimental contaminant at higher concentrations can be non-toxic and/or without consequence to the cleaning efficiency of the cleaning solution at lower concentrations.

Further, the cleaning solution may include at least one component selected from the group consisting of antibiotics, antiviral agents (for example, peroxide generating agents such as EXACT™ [e.g., trademarked haloperoxidase products marketed by ExOxEmis, Inc., San Antonio, Tex.], hydrogen peroxide, permeation enhancers (for example, fatty acid esters, such as laurate, myristate and stearate monoesters of polyethylene glycol), organic acids (for example, citric acid) or dilute solutions of strong acids (for example, hydrochloric acid).

It is advantageous to clean bones using at least two separate solutions of the invention. For instance, a first cleaning solution can include, at a concentration of about 0.01× of the 1× a detergent solution. After the first solution is applied to the bone, a second solution may be used for flushing the first solution from the bone and for further reducing bacterial, fungal or viral contaminants. Preferably, the second solution includes at least one component selected from the group consisting of endotoxin-free deionized/distilled water and ethanol. Further, the second solution may include at least one component selected from the group consisting of antibiotics, antiviral agents, hydrogen peroxide, permeation enhancers, organic acids and dilute solutions of strong acids.

The solutions of the invention are preferably controlled within a temperature range of 20° C. to 65° C. and maintained within the temperature range during processing. More preferably, the temperature range is controlled and maintained at about 27° C. to 55° C. Even more preferably, the temperature range is controlled and maintained at about 40° C. to 48° C.

The compositions of the invention are useful with any type or size of bone, in whole or in part. Although the examples below describe use of the invention on "large" bone grafts, the compositions of the invention are also useful for the cleaning of any bone or portion of bone, regardless of size. Further, the examples are directed especially to human cadaveric bones, but it should be understood that the invention is equally applicable to bones obtained from other species.

As used herein, the terms "bone" or "bone graft" may be used interchangeably, and include whole, intact bones, regardless of size, or substantial parts of a whole bone. Practically speaking, bones or bone grafts, as defined herein may include the range of whole bones down to pieces at least as small as 1–5 cm. Examples of whole bones include (but are not limited to) femur, tibia, ilia, humerus, etc., prior to subsequent processing into specific grafts.

The composition of the invention is viricidal towards enveloped viruses such as the HIV, hepatitis, and herpes viruses, for example. Further viruses which have been killed by the instant compositions include measles virus, togavirus, enterovirus, rhinovirus, rubella virus, reovirus, respiratory syncytial virus, cytomegalovirus, Epstein Barr Virus, Vesicular Stomatitis Virus, vaccinia virus, rabies virus, influenza virus, parainfluenza virus, adeno-associated virus, lymphoma virus, human papovirus, and lymphocytic choriomeningitis virus, for example.

It is possible to monitor the solution exiting the bone cavity to determine when essentially all of the bone marrow has been removed from the bone. Monitoring methods include, but are not limited to, measuring absorbance substantially at 410 nm, and visual monitoring of the color of the solution exiting the bone.

Other methods of determination of the degree to which the bone marrow has been removed from the bone graft include: taking core samples of bone plugs, solubilizing bone marrow in the bone plug core samples using sodium hydroxide and taking a protein assay of the same. Visual inspection of the trabecular bone can be examined using a scanning electron microscope. Gross visual examination can be performed by cutting the graft open for visual inspection by the naked eye or with a stereoscope, for example.

Bone Cleaning Process in which the Compositions of the Invention may be used

The compositions of the invention may be used in a variety of bone cleaning procedures. For instance, the solutions may be utilized in conventional flushing procedures to remove bone marrow, which entails a pressurized flow of solution as a rapidly moving stream which dislodges bone marrow by impact of the solvent on the bone graft.

The compositions may also be used in a process such as the following. Bone materials procured from cadaveric donors, such as large, essentially whole, bone grafts, are thawed under sterile conditions at room temperature. The bone is then debrided of external soft tissues. This debridement includes removal of excess cartilaginous tissues on the proximal and distal ends of bones at their articulation surfaces.

After debridement, a hole is made substantially midway between the distal and proximal ends of the bone. The hole may be formed by drilling, and is preferably formed to have an outside diameter of approximately ¼ to ⅝ inch. The hole need only be drilled deep enough to penetrate the cortical bone to enable a tapping port to be securely inserted into the hole. After removing as much bone marrow as possible, a vacuum line is attached securely at one end to the tapping port after insertion of the tapping port into the hole.

The opposite end of the vacuum line is securely attached to a disposable container, via an inlet tube. The inlet tube is sealingly connected to a disposable container by a stopper means. The stopper means is preferably a rubber stopper, but any equivalent, such as, a cork stopper, may be used to seal the inlet tube within the disposable container.

An outlet tube of the disposable container is securely attached to another vacuum line. At the opposite end, the vacuum line is attached to a vacuum source which is capable of drawing a vacuum in the range of about 5 mm to 60 mm Hg on the entire apparatus. The vacuum source used to draw solution through the bone grafts will be set to draw a vacuum between about 15 and 35 mm Hg with the preferred range being about 20 and 30 mm Hg.

After connection of the vacuum apparatus, the bone is immersed into a solvent containing one of the compositions of the invention, contained within an open container. The vacuum source is next turned on to draw the solution through the articulation surfaces which have been debrided of cartilage, through the cancellous bone structure and through the intermedullary canal of the bone.

As mentioned above, the vacuum drawn is set between about 15 and 35 mm Hg with the preferred range being between about 20 and 30 mm Hg. The actual vacuum level is adjusted such that the flow rate of solution through the bone graft does not occur so rapidly that the bone marrow is not effectively solubilized, but rapidly enough to effectively remove solubilized bone marrow. Flow rates of solvent should range between about 8 and 32 ml per minute with the preferred rates being between about 15 and 25 ml per minute.

The solution enters the bone through the ends at the cartilaginous surfaces. Restricted flow of the solution through the cartilaginous ends of the bone minimizes mechanical and/or structural damage to the cancellous bone by causing a slow flow rate of solvent through the trabecular bone space occupied by bone marrow. As the solution is drawn through the bone, it can be collected in a disposable container. Because the aspirate solution is largely liquid phase, the solution is deposited into the disposable container as the vacuum is drawn through the inlet tube end out the outlet tube.

The process may optionally include refilling the container with a second solution for further processing the bone including flushing the first solution from the bone. The second solution is drawn through the cartilaginous articulating surface and then through the bone cavity and the vacuum line to exit the bone at the opening.

The solution is collected in the disposable container and is initially dark red, reflecting a saturated or nearly saturated solution of marrow. As the process continues, the solution gradually turns to a color similar to that of serum as bone marrow is removed from the graft. By sampling the effluent material being removed from the bone, such as by a sampling port accessible by use of a syringe, it is possible to monitor completion of bone marrow removal by measuring absorbance at 410 to 700 nm. By this method, it is possible to determine when essentially all of the bone marrow is removed from the bone graft. Bone marrow solubilization and cleaning of the bone is essentially complete when eluent protein concentration reaches a minimal, substantially stable value.

After it has been determined that essentially all of the bone marrow has been removed from the bone (i.e., the bone graft) the bone is removed from the container and the solution can be replaced with a second solution. The bone is then immersed in the second solution in the container, for further processing. The second solution to be drawn through the bone graft may include endotoxin-free deionized/distilled water, ethanolic solutions of water, or isotonic saline in endotoxin-free deionized/distilled water. During addition of the second solution to the container, the vacuum can be shut off until processing of the second solution through the bone is ready to resume.

The second solution is drawn through the bone in order to reduce the amount of the first solution in the bone graft and/or to deliver additional agents to be used in processing of the whole bone graft. For example, addition of ethanol (50% to 100%, vol to vol) to reduce bacterial, fungal and/or viral contaminants which might be present in the bone graft. The use of absolute (100%) ethanol in the second solution would further serve to dehydrate the bone, reducing subsequent times needed for freeze-drying.

Since the flow of solution through the bone graft will be less restricted during flushing with the second solution, the level of vacuum used is appropriately reduced to maintain an appropriate flow rate, preferably between 10 and 15 ml per minute.

The volume of the second solution which is drawn through the bone varies depending on the size of the bone being processed, the volume of the intermedullary canal of the bone being processed, and the concentration of detergent and/or ethanol used in the first solution, but in general should approximate a volume 10-fold greater than the volume of the bone graft being processed.

Following completion of flushing of the bone graft with the second solution, the bone graft may be removed from the container and processed into smaller bone grafts via procedures previously established for the production of such grafts.

The following illustrative examples describe the instant invention in more detail. However, they are not intended to limit the scope of the specification and claims.

EXAMPLES

Example 1

A femur was thawed, debrided of excess soft tissue (including the excess cartilage present on the articulating surfaces) and a hole approximately ¼ to ⅝ inch outside diameter was drilled in the bone shaft approximately midway between the distal and proximal ends of the bone. The hole was only drilled deep enough to penetrate the cortical bone so that intramedullary bone marrow could be flushed from the bone and so a tapping port could be securely inserted into the hole. The vacuum line was attached securely to the tapping port.

Two liters of a solution of 10% ethanol in a 0.01× solution containing 0.0066 weight percent Brij-35, 0.002 weight percent Nonidet P-40, and 0.002 weight percent Nonoxynol-9 in endotoxin free water were added to an open container in a clean room environment under sterile conditions. The femur having the vacuum line attached via the tapping port was then placed into the container, and immersed towards the bottom of the container.

The temperature of the cleaning solution was adjusted to 45° C. prior to addition of the bone graft. A vacuum was applied to the system and maintained in the range of 25 to 27 mm Hg. The flow rate of solution through the bone graft was maintained at approximately 10 ml per minute by adjusting the vacuum. The solution collected in the disposable container was dark red initially, turning to a color similar to that of serum as bone marrow was removed from the graft. By sampling the effluent material being removed from the bone graft, via a sampling port accessible by use of a syringe, it was possible to monitor completion of bone marrow removal by measuring absorbance at 410 nm, to determine when essentially all of the bone marrow was removed from the bone graft. After drawing two liters of first solution through the bone graft, the vacuum to the system was discontinued and the open container was refilled with one liter of endotoxin-free deionized/distilled water. The vacuum was reapplied to the system. The deionized/distilled water was flushed through the bone graft at approximately 15 ml per minute to remove the detergent solution. Following the flushing of detergent solution from the bone graft, vacuum was discontinued to the system and the bone graft was removed from the open container, after which the vacuum line and tapping port were removed. The bone graft was then ready for further processing into small bone grafts as required.

Example II

A femur was thawed, prepared and cleaned in the same manner as indicated in Example I, with the following exceptions. The bone was cut in half using a bone saw. Tie proximal end of the femur was used in this example, however, the distal end of the femur would be similarly processed. Pulsavac lavage was applied to remove bone marrow from the luminal space. One liter of solution of 10% ethanol in a 0.01× solution container 0.0066 weight percent Brij-35, 0.002 weight percent Nonidet P-40, and 0.002 weight percent nonoxynol-9 in endotoxin free water was added. A sealing cap was placed over the cut end of the bone graft and secured using a clamping device. A vacuum line was attached securely to an access line in the sealing cap.

The bone graft having the vacuum line attached via the sealing cap and access line was then placed into the container, and immersed towards the bottom of the container. The temperature of the cleaning solution was adjusted to room temperature (approximately 27° C.) prior to addition of the bone graft. Vacuum was applied to the system and maintained in the range of about 25 to 27 mm Hg. The flow rate of solution through the bone graft was maintained in the range of about 25 to 27 mm Hg. The flow rate of solution through the bone graft was maintained at approximately 10 ml per minute by adjusting the vacuum.

The solution collected in the disposable container was initially dark red, and turned to a color similar to that of serum as bone marrow was removed from the graft. By sampling the effluent material being removed from the bone graft, via a sampling port accessible by use of a syringe, it was possible to monitor completion of bone marrow removal by monitoring absorbance at 410 nm, and it was possible to determine when essentially all of the bone marrow was removed from the bone graft.

After drawing one liter of first solution through the bone graft, the vacuum to the system was discontinued and the open container was refilled with one liter of endotoxin-free deionized/distilled water (second solution), after which vacuum was reapplied to the system. The deionized/distilled water was flushed through the bone graft at approximately 15 ml per minute to remove the detergent solution. Following the flushing of detergent solution from the bone graft, vacuum was discontinued to the system and the bone graft was removed from the container. Next, the sealing cap and vacuum line were removed. The bone graft was then ready for further processing into small bone grafts as required.

Although the invention has been described with reference to particular means, materials and embodiments, it is to be understood that the invention is not limited to the particulars disclosed and extends to all equivalents within the scope of the claims.

All the references cited above are incorporated herein in their entirety by reference.

I claim:

1. A composition effective for the cleansing of mammalian bones and particularly the removal of bone marrow and like blood deposits therefrom said composition being an aqueous solution comprising:
    i) about 0.066 wt. % polyoxyethylene-23-lauryl ether,
    ii) about 0.02 wt. % poly (ethylene glycol)-p-nonyl-phenyl-ether,
    iii) about 0.02 wt. % octylphenol-ethyleneoxide, and
    iv) water,
    wherein said composition does not contain a membrane stabilizer.

2. A composition effective for the cleansing of mammalian bones and particularly the removal of bone marrow and like blood deposits therefrom said composition being an aqueous solution consisting essentially of:
    i) about 0.066 wt. % polyoxyethylene-23-lauryl ether,
    ii) about 0.02 wt. % poly (ethylene glycol)-p-nonyl-phenyl-ether,
    iii) about 0.02 wt. % octylphenol-ethyleneoxide, and
    iv) water.

3. A composition effective for the cleansing of mammalian bones and particularly the removal of bone marrow and like blood deposits therefrom said composition being an aqueous solution consisting of:
    i) about 0.066 wt. % polyoxyethylene-23-lauryl ether,
    ii) about 0.02 wt. % poly (ethylene glycol)-p-nonyl-phenyl-ether,
    iii) about 0.02 wt. % octylphenol-ethyleneoxide, and
    iv) water.

4. A kit for cleaning a bone for a bone graft, comprising an aqueous solution consisting essentially of:
    i) about 0.066 wt. % polyoxyethylene-23-lauryl ether,
    ii) about 0.02 wt. % poly(ethylene glycol)-p-nonyl-phenyl-ether, and
    iii) about 0.02 wt. % octylphenol-ethyleneoxide,
    wherein said solution does not contain a membrane stabilizer.

5. A composition for cleansing mammalian bone, comprising:
    i) polyoxyethylene-23-lauryl ether;
    ii) poly (ethylene glycol)-p-nonyl-phenyl-ether;
    iii) octylphenol-ethyleneoxide, and
    iv) water, wherein said polyoxyethylene-23-lauryl ether, poly(ethylene glycol)-p-nonyl-phenyl-ether, and octylphenol-ethyleneoxide, are present in a weight percent ratio of 3.3:1:1, respectively.

6. A composition effective for cleansing mammalian bones and for removing bone marrow and blood deposits therefrom, said composition being an aqueous solution, comprising:

a protein solubilizing detergent;

one or more lipid solubilizing detergents; and water, wherein said protein solubilizing detergent is present in said aqueous solution at from about 0.001 to about 2.00 weight percent, and said lipid solubilizing detergent is present in said aqueous solution at from about 0.001 to about 2.00 weight percent.

7. The composition of claim 6, wherein said protein solubilizing detergent is present in said aqueous solution at from about 0.01 to about 0.5 weight percent, and said lipid solubilizing detergent is present in said aqueous solution at from about 0.01 to about 0.5 weight percent.

8. The composition of claim 7, wherein said protein solubilizing detergent and said lipid solubilizing detergent are present in said aqueous solution at a weight percent ratio of about 1.65:1.

9. The composition of claim 6, wherein said protein solubilizing detergent is selected from the group consisting of: polyoxyethylene (9) lauryl ether; ployoxyethylene (9) lauryl ether; dodecylmaltoside lauryl maltoside; decaoxyethylene monolauryl ether; octaethylene glycolisotridecyl ether; polyoxyethylene (8) isotridecyl ether; polyoxyethylene (10) isotridecyl ether; PEG (10) tridecyl ether; sodium lauryl sulfate; and sodium dodecyl sulfate.

10. The composition of claim 6, wherein said lipid solubilizing detergent is selected from the group consisting of: poly(ethylene glycol)-p-nonyl-phenyl-ether; octylphenol-ethyleneoxide; a polyoxyethylene alcohol; a polyethylene glycol pisooctylphenylether; a polyoxyethylene ester, 1-argitol; polyoxyethylene nonylphenol; and a polyoxyethylene sorbitol ester.

* * * * *